United States Patent
Yancey et al.

(10) Patent No.: US 6,739,194 B1
(45) Date of Patent: May 25, 2004

(54) METHOD OF DETERMINING PHYSICAL PROPERTIES OF WOOD

(75) Inventors: Michael J. Yancey, Puyallup, WA (US); Tom J. Taylor, Seattle, WA (US)

(73) Assignee: Weyerhaeueer Company, Federal Way, WA (US)

( * ) Notice: Subject to any disclaimer, the term of this patent is extended or adjusted under 35 U.S.C. 154(b) by 0 days.

(21) Appl. No.: 10/608,380

(22) Filed: Jun. 27, 2003

(51) Int. Cl.[7] ................................................ G01N 29/18
(52) U.S. Cl. ............................................ 73/579; 73/597
(58) Field of Search ......................... 73/579, 597, 598, 73/594, 12.11

(56) References Cited

U.S. PATENT DOCUMENTS 5,251,491 A * 10/1993 Nakaoka et al. ............... 73/579
6,026,689 A * 2/2000 Snyder et al. ................. 73/597
2003/0216829 A1 * 11/2003 Andrews et al. ............... 73/579

* cited by examiner

Primary Examiner—John E. Chapman (57) ABSTRACT

A method is described for determining a physical property of a log or similar wood member. A small amount of a liquid or solid is projected against the end of the log with sufficient energy to induce a stress wave. Water is a preferred liquid and an ice pellet is the preferred solid material. A water pulse of about 40 g or less shot from a distance of about 1.2 m with about 9–10,000 kPa pressure will induce a useful shock wave. Similarly an ice pellet weighing 5–10 g shot from the same distance at about 400–500 kPa has given excellent results. The travel time of the stress wave may be measured by an accelerometer in contact with the log. Alternatively, a laser Doppler vibrometer aimed at the log end can record the travel time. The use of the method obviates the need for a mechanical hammer striking the log as well as the requirement for the logs to be even ended at the test location.

12 Claims, 6 Drawing Sheets

METHOD OF DETERMINING PHYSICAL PROPERTIES OF WOOD

The present invention relates to a nondestructive method for determining at least one physical property of a wood member. It further relates to a method of optimizing value of the wood member during further processing

BACKGROUND OF THE INVENTION

It has been long known to use nondestructive testing methods for determining some physical property of a wood member which relates to its strength or soundness. Items such as logs, utility poles, or lumber intended for engineering applications are routinely tested. One means of doing this is to induce a stress wave within the material and note a response characteristics; e.g., the time of travel of the wave, to infer the property being studied. The stress wave may be induced by striking the material with a hammer and noting the response by means of an accelerometer in contact with the piece. Another way is to direct a sonic pulse at the material, either by a transducer in direct contact, or by an external transducer through an air gap. The sonic pulse may be swept through a range of frequencies since the impedance of the wood is high to any but frequencies at or very near the resonance point, or to harmonics of this frequency. Unfortunately, the energy delivered by the sonic pulse is relatively low and the resulting stress wave in the log may be difficult to detect and process.

A number of earlier investigators have looked at varying means of using sonic pulses to determine physical properties of wood members. An example is found in published PCT Application WO 02/08747 to Harris. Unfortunately, in systems using sonic pulses the sound may be very loud. At best the noise can be an annoyance. It may require those working nearby to wear ear protection in order to prevent hearing damage.

Systems using mechanically induced shock waves that measure end-to-end transit time of the wave in the sample have been in use for evaluating logs and assigning them for optimum use based on the determined elastic modulus. Such a system is described in Snyder et al, U.S. Pat. No. 6,026,689. The system is normally employed on a log ladder in a sawmill or merchandiser. With this method the logs must be even ended for access to the pneumatic hammer. It is also necessary for the log to remain stationary for the short time required for the test. The need for the logs to be even ended poses some difficulty since the heavy logs, which are frequently of varying lengths, must be brute force adjusted into the proper position All of the systems noted above suffer some deficiency when used in an industrial environment such as a sawmill or log sort yard. These environments have inherently high background noise. This greatly complicates the use of non-contact systems and makes detection of the weak stress wave induced in the log extremely difficult to separate from the noise. Even-ending of the logs for access to a pneumatic hammer poses a considerable and sometimes insolvable problem Further, the logs are often moving at a high rate of speed and the time window in which a reading may be made is frequently considerably less than a second. The present invention is an improvement in the known systems and successfully overcomes many of the problems just noted.

SUMMARY OF THE INVENTION

The present invention is a non-contact method for determination of one or more physical properties in a wood member such as a log or structural timber. When the term "log" is used, it is a term of convenience and should be read with sufficient breadth to include any elongated wood member being tested for structural properties.

The method employs projecting a small amount of a liquid or solid against the end of the log with sufficient energy to initiate a stress wave. By small amount is meant generally less than about 50 g. The term "projecting" implies travel through space for a distance in the range of about 0.3–3 m (1–10 ft). The time of travel of the stress wave to the end of the log and back may be measured by an accelerometer or other suitable transducer in contact with the log. Alternatively, a non-contact transducer such as a laser Doppler vibrometer may be used to receive the returned signal. The returned signal is converted into the frequency domain and the resonant frequency of the log is determined.

The speed of the stress wave transmitted into the log can be readily determined by the equation $S=2Lf$, where L is the length of the log and f is the resonant fundamental frequency. Stress wave speed is known to relate directly to modulus of elasticity (MOE), with lower speeds indicating a lower MOE. Knowledge of the MOE can then be used to determine subsequent use of the log. Low modulus logs can be sawn into dimension lumber sizes or grades where bending strength is not critical or can even be directed for production of pulp chips or composite panels. U.S. Pat. No. 6,026,689 is descriptive of how knowledge of MOE can be used to maximize product value of saw logs.

A high pressure pulse of water is an example of a benign liquid that may be projected against the end of the log to initiate the stress wave. By high pressure is meant at least about 3450 kPa (500 psi), more preferably at least about 8300 kPa (1200 psi). Other liquids are suitable but water is preferred. While various equipment arrangements are possible to create the high pressure water pulse, they will in general have the common elements of a high pressure pump, an accumulator to hold the requisite amount of high pressure air, a container to store the amount of water needed, a valve to release the air from the accumulator and project the water, and a nozzle or similar orifice to direct the water at the target. A small ice pellet is a preferred example of a solid material that may be directed at the end of the log to initiate the stress wave. Other solid materials may be used as pellets but ice is much preferred. The ice pellet will fragment when it hits the log and generally adhere for a short period of time. There is no need for recovery of the pellets, as with other solid materials, and the ice fragments readily dissipate into the use environment.

It is an object of the present invention to provide an improved method for evaluation of at least one physical property of a wood member.

It is a further object to provide a method using a high pressure liquid pulse to excite resonance within such a member.

It is also an object to direct a small ice pellet at the end of the member to initiate the stress wave.

It is another object to provide a method for non-destructive evaluation of a wood member on a log ladder that does not require the logs to be even ended for testing.

It is one more object to provide a fully non-contact method for determination at least one log physical property.

These and many other objects will become readily apparent upon reading the following detailed description taken in conjunction with the drawings.

DETAILED DESCRIPTION OF THE PREFERRED EMBODIMENTS

The operation of the method will now be explained in detail. While this example describes a sawmill environment, this is in no way intended to be limiting since the applicability of the method in many different uses is evident. As an example, it may be assumed that the necessary apparatus is installed in conjunction with a log ladder where logs to be sawn are fed into the sawmill from an outside source. The log ladder is a conveyor in which logs are carried side-by-side in parallel fashion. There is no need for the logs to be even ended facing the apparatus. An actuator directs the high pressure liquid pulse or solid pellet at the log end to initiate the stress wave. The received signal may be detected by a transducer, such as an accelerometer, in actual contact with the log. Alternatively, a laser Doppler vibrometer aimed at the log end is a useful non-contact instrument to detect the reflected stress wave. The detected signal is fed to an analog to digital converter where it converted from the time domain into the frequency domain This information, in turn, is sent to the stress wave velocity computer where the stress wave velocity is calculated. Since stress wave velocity is related to stiffness, the velocity may be readily converted to modulus of elasticity. In turn, the stress wave velocity or stiffness value is sent back to the mill programmable logic controller. From there it may be used in a cutting optimizer program which determines how the log should be sawn or otherwise utilized for maximum product value. U.S. Pat. No. 6,026,689 describes such a program that is used in conjunction with a mechanical hammer to actuate the stress wave.

It is known that the resonant frequency is primarily affected by log length and density, the density typically being closely related to species. Diameter is a minor factor that can usually be neglected. Moisture content will affect density somewhat.

EXAMPLE 1

Figure 1:
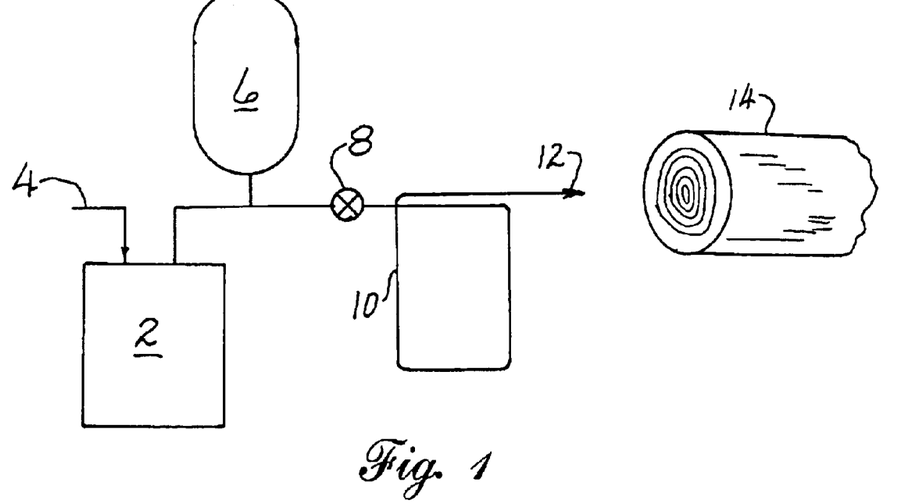
FIG. 1 is a block diagram showing essential elements required for the present method using a liquid pulse.

In an initial experiment to determine practicality of the use of a water pulse, the following equipment was used in the arrangement shown in FIG. 1. The air intensifier/amplifier 2 chosen was a model DLA-30-1-UV-M made by Maxpro Technologies, Erie, Pa. This generated an air pressure of about 10,350 kPa (1500 psi). The intensifier was supplied with air from a source 4 and held in an accumulator 6. It was also connected through valve 8 to a loop of metal tubing 10 in the form of a rectangle, approximately 10×20 cm (4×8 in), which served as a water reservoir. The tubing loop was manually disconnected from the valve and filled with the desired amount of water before each trial. Tubing loops having inside diameters of 3.2, 6.4, and 9.5 mm (⅛, ¼ and ⅜ in) were used to vary the discharge characteristics; e.g., velocity and mass flow rate. The tubing extended beyond the end of the loop 10 to serve as a nozzle 12. The ball valve 8 between the intensifier and loop was manually operated to release the water pulse.

The test log 14 species was western hemlock (*Tsuga heterophylla*) and the log had a length of ~3.5 m (11½ ft) and a butt end diameter averaging about 0.46 m (18in). The nozzle 10 of the water pulse projector was about 1.2 m (4 ft) from the end of the log. A stress wave sensor, not shown, was in contact with the opposite end of the log except for those experiments noted where this location was changed. This was a Model 8702B50 accelerometer supplied by Kistler Instruments Corp, Amhurst, N.Y. It will be understood that this is not an endorsement of the above or any other equipment noted since fully equivalent devices are available from other suppliers. Air pressure was 10340 kPa (1500 psi) unless otherwise noted.

Tables 1–3 show the results of these initial experiments. The hammer taps served as a control experiment using a common ball peen hammer to hit the end of the log and initiate the stress wave.

TABLE 1

Initial Water Pulse Experiments

| Tube Diam., mm | Time Trace Peak, G[1] | Frequency, Hz | Response Power, mG[2] | Notes |
|---|---|---|---|---|
| — | 13.5 | 617 | 38 | Hammer - light |
| — | 25.5 | 621 | 60 | Hammer - medium |
| — | 36.5 | 622 | 101 | Hammer - heavy |
| 3.2 | 0.36 | 620 | 3.1 | — |
| 6.4 | 0.78 | 619 | 10.5 | — |
| 9.5 | 0.83 | 619 | 5.9 | — |
| 9.5 | 4.5 | 619 | 12.4 | Increased water volume |
| 9.5 | Poor signal | Poor signal | Poor signal | 10 mL water |
| 9.5 | 1.9 | 617 | 11.5 | 20 mL water |
| 9.5 | 4.5 | 617 | 11.5 | 30 mL water |
| 9.5 | 1.8 | 616 | 11.7 | 40 mL water |

[1]Force in gravitational units.
[2]Force in milligravitational units root mean squared.

While the signal response was much lower using the water pulse excitation compared with striking with a hammer, the results measuring the resonant frequency were essentially identical showing the full practicality of the technique.

A set of experiments similar to those above was then made but with the accelerometer in contact with the side of the log The accelerometer was placed 35 and 76 cm back from the end of the log with the axis of the accelerometer parallel to the longitudinal axis of the log. Results of these tests are shown in Tables 2 and 3.

TABLE 2

Initial Water Pulse Experiments
Acceler meter 35 cm from End of Log
8960 kPa (1300 psi) Air Pressure

| Tube Diam., mm | Time Trace Peak, G[1] | Frequency, Hz | Response Power, mG[2] | Notes |
|---|---|---|---|---|
| — | 1.3 | 623 | 8.7 | Hammer - light |
| — | 2.4 | 622 | 12.8 | Hammer - medium |
| — | 10.0 | 621 | 38 | Hammer - heavy |
| — | 16.0 | 621 | 54 | Hammer - ex. heavy |
| 9.5 | 0.8 | 622 | 3.5 | — |

[1]Force in gravitational units.
[2]Force in milligravitational units root mean squared.

TABLE 3

Initial Water Pulse Experiments
Accelerometer 76 cm Back from End of Log
10350 kPa (1500 psi) Air Pressure

| Tube Diam., mm | Time Trace Peak, G[1] | Frequency, Hz | Response Power, mG[2] | Notes |
|---|---|---|---|---|
| — | 1.7 | 619 | 6.7 | Hammer - light |
| — | 2.4 | 620 | 7.8 | Hammer - medium |
| — | 13.3 | 618 | 32 | Hammer - heavy |
| — | 33.0 | 619 | 44 | Hammer - ex. heavy |
| 9.5 | 2.6 | 619 | 3.6 | — |

[1]Force in gravitational units.
[2]Force in milligravitational units root mean squared.

It is again apparent that position of the accelerometer position is not critical and that resonant frequency determined by use of a water pulse is essentially identical to that determined by using hammer blows.

EXAMPLE 2

Figure 3:
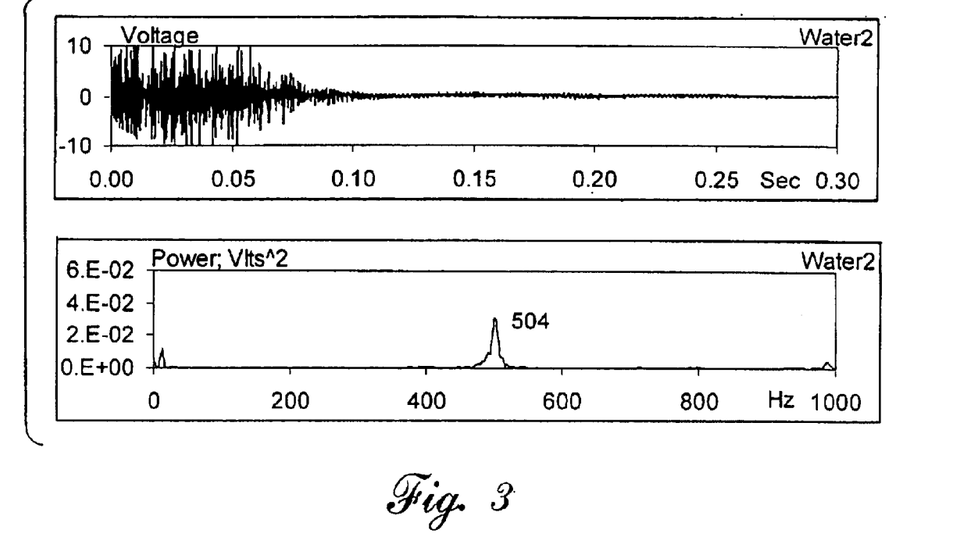
FIG. 3 shows the response curve measured by an in-contact accelerometer using a water pulse to initiate the stress wave.

The practicality of the method having been shown, the experiment of Example 1 was repeated using different equipment. The original air intensifier was replaced by a Campbell Hausfeld airless paint sprayer, Paint Pro Series, available from Campbell Hausfeld, Harrison, Ohio. This device generated a useful pressure of 19,300 kPa (2800 psi). The tubing loop originally used as an accumulator was replaced with a Purrrrr-O-Lator, Model P1000, accumulator. Purrrrr-O-Lator is a trademark of and is available from Cat Pump, Minneapolis, Minn. The test piece was a green Douglas-fir log having a length of ~3.5 m (11.6 ft), a major end diameter of 0.35 m (14 in) and a minor end diameter of 0.30 m (12 in). Experience has shown that the average resonant frequency for a log of this species and length would be expected to fall within the range of about 350–650 Hz. The volume of the ejected water pulse was about 40 mL and the distance between the nozzle and log again about 1.2 m (4 ft). The ring down voltage measured by the accelerometer in contact with the log is seen as the upper graph in FIG. 3 and this signal converted to resonant frequency is shown as the lower graph. A frequency of 504 Hz was determined. This is somewhat lower than would be expected from other measurements made on the same lop, However, it is within an acceptable range of variation.

Figure 4:
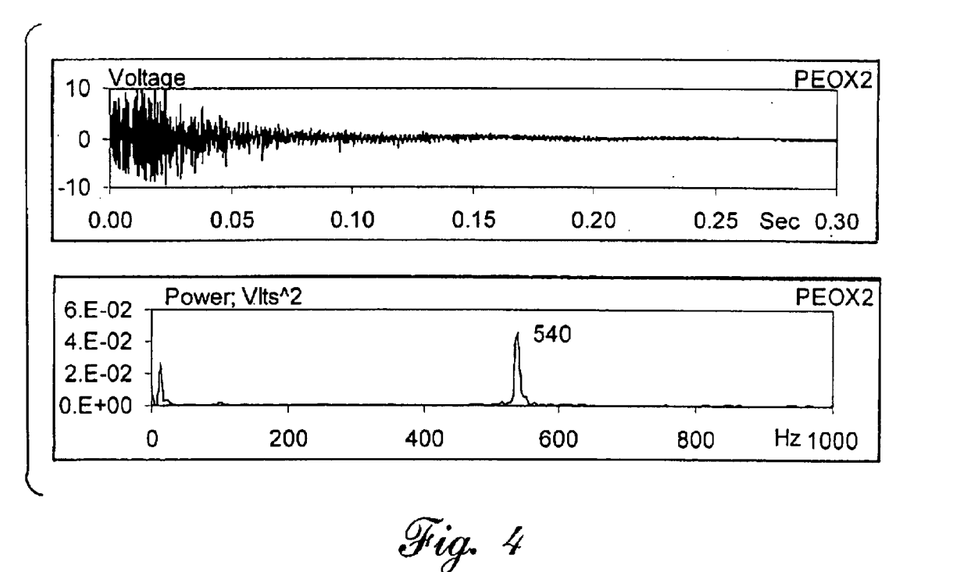
FIG. 4 is similar to FIG. 3 but with the liquid pulse being water containing a non-ionic surfactant.

It is desirable to keep the water pulse well collimated so that the impact area and force delivery time are minimized. One way in which this could be accomplished was to reduce the viscosity of the water by inclusion of a surfactant. To this end polyethylene oxide (Polyox WSR 308, Dow Chemical Co., Midland, Mich.) was added to the water in a concentration of 0.1% Test conditions were otherwise the same as those just noted above. The ring down voltage and resultant resonant frequency graphs are seen in FIG. 4. The resonant frequency of 540 Hz was in excellent agreement with that predicted from earlier measurements. The inclusion of the surfactant appeared to be of benefit in increasing water pulse efficiency and measurement accuracy.

EXAMPLE 3

Figure 2:
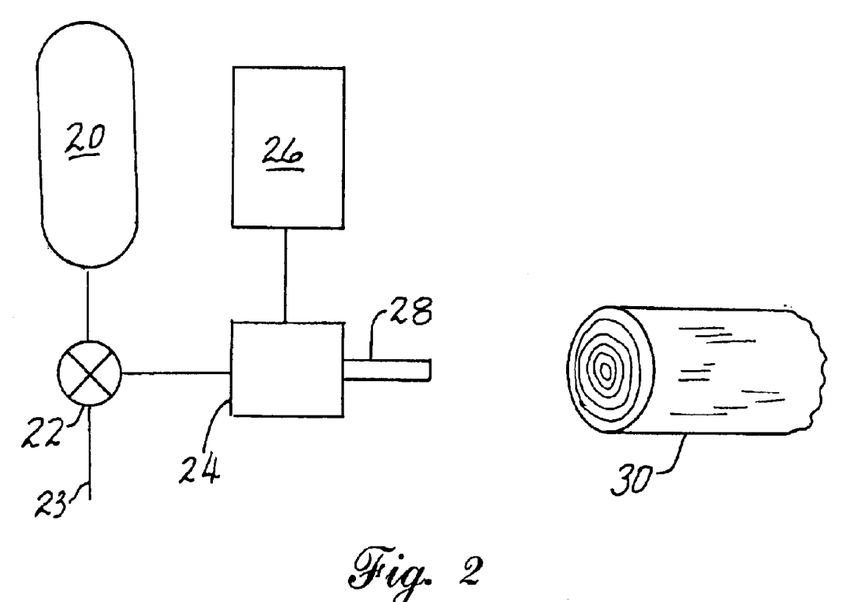
FIG. 2 is a similar block diagram showing the elements for directing a solid pellet at the log end.

One problem with the water pulse was the relatively low signal level seen by the accelerometer when compared with the conventional pneumatic hammer as the activation source. A new experiment was devised in which an ice pellet was shot at the end of the log. Ice was chosen as preferable to other solid materials since it would dissipate harmlessly in the environment and would not need to be collected for reuse. An apparatus was constructed as seen in FIG. 2. An accumulator 20 is attached to a three-way valve 22 and receives relatively low pressure air from line 23. A line from valve 22 is connected to a shutter/magazine device 24 which receives ice pellets from a source 26. When valve 22 is opened to direct the accumulated air to shutter/magazine 24, the pellet is shot through tube 28 to impact the end of log 30. Ice pellets were made in a weight range of about 5–10 g although the weight is not critical. A 5 g pellet is about 19×19 mm in dimensions. Air pressure was 415 kPa (60 psi). The accumulator has a volume of 2.25 L and is available form Swagelok, Solon, Ohio, as Type 304L-HDF-2250. Three-way valve 22 was manufactured by Mac Valves, Inc., Wixom, Mich. as Type 56C-67-00000.

Figure 5:
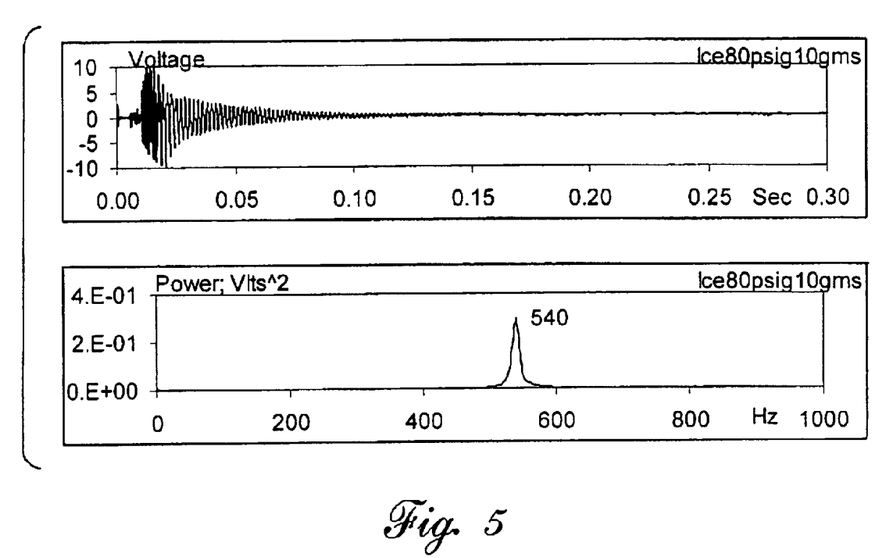
FIG. 5 shows the response curve measured by an in-contact accelerometer for a 10 g ice pellet shot at 550 kPa (80 psig).

FIG. 5 shows the ring down voltage and resultant resonant frequency measured when a 10 g ice pellet was shot at 550 kPa (80 psi) over a distance of about 1.2 m (4 ft). A strong sharp signal was induced in the log and the resonant frequency was determined to be 540 Hz, exactly as expected.

Figure 6:
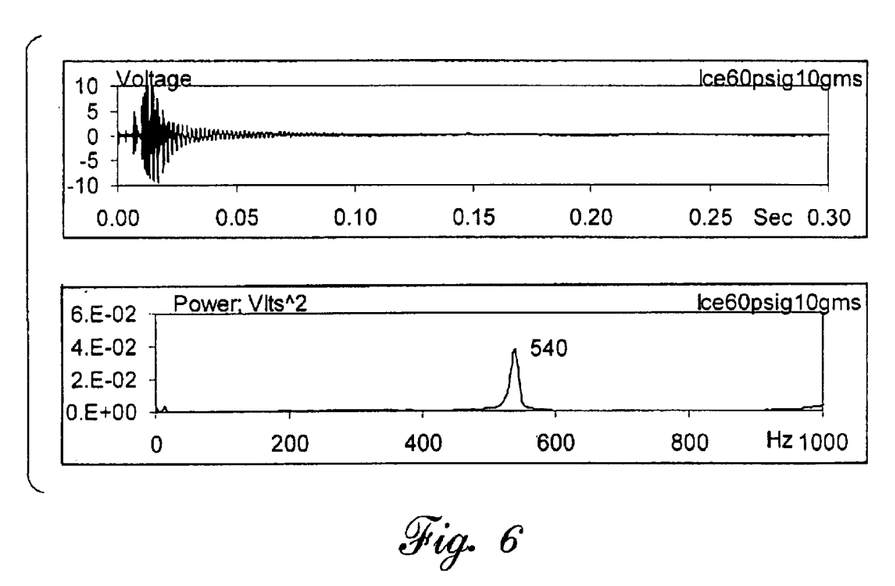
FIG. 6 is similar to FIG. 5 but with the pressure reduced to 415 kPa (60 psig).

FIG. 6 was a repeat of the experiment of FIG. 5 with the difference that a 10 g pellet was shot at the lower pressure of 415 kPa (60 psi). Results were identical and again, a sharp signal resulted.

FIG. 7 was again similar to the conditions described for FIG. 6 but the ice pellet weight was reduced from 10 g to 5 g. The results were completely satisfactory with the resonant frequency as expected.

Figure 7:
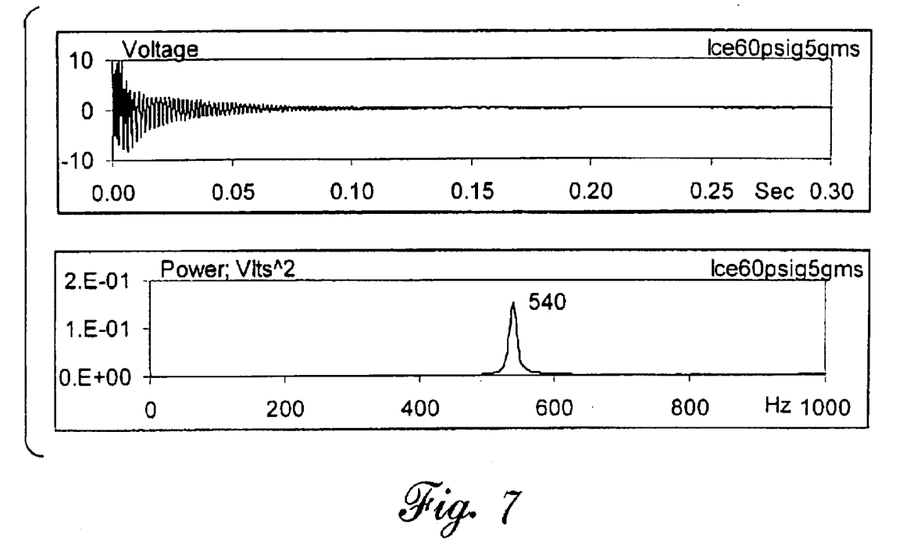
FIG. 7 shows the response curve for a 10 g ice pellet shot at 415 kPa (60 psig).
Figure 8:
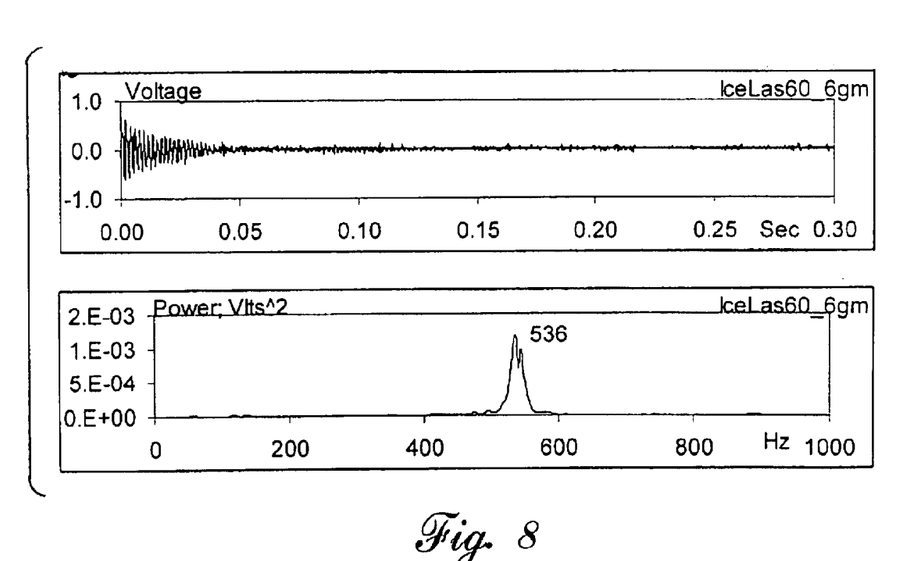
FIG. 8 shows the response using a 6 g ice pellet shot at 415 kPa (60 psig) at a stationary log using a laser Doppler vibrometer to determine stress wave response time.

In the experiments shown in FIGS. 5–7 an accelerometer was in contact with the far end of the log to detect the stress wave. In order to see if a fully non-contact method could be used the accelerometer was replaced by a laser Doppler vibrometer. The instrument used was obtained from Polytec PI, Tustin, Calif., as a Type PDV-100. This was aimed at the end of the log impacted by the ice pellet The ice pellet weighed 6 g and was shot at a pressure of 415 kPa (60 psi). Ring down and resonant frequency results are seen in FIG. 8. The results were quite satisfactory, again with the resonant frequency measured being in close accord with that of other methods.

Figure 9:
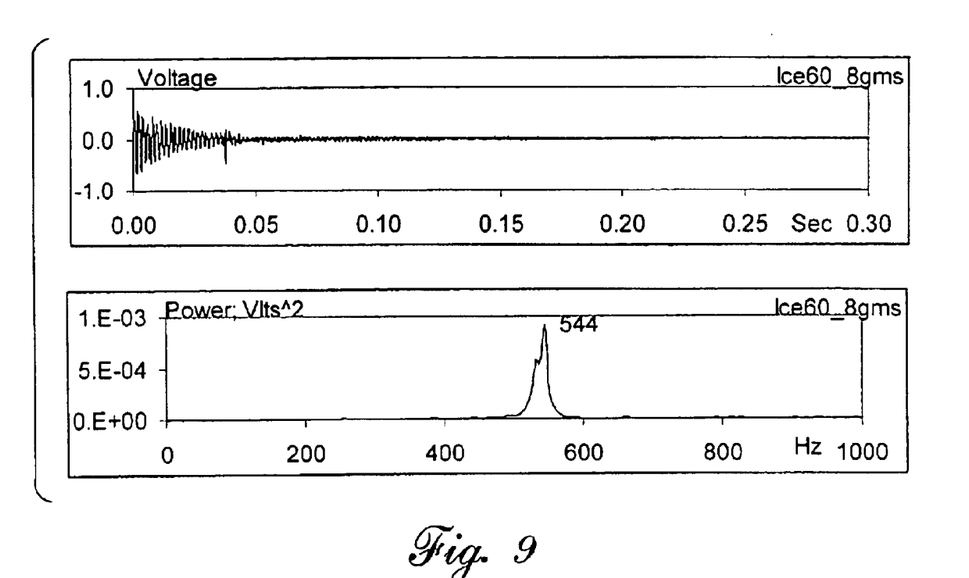
FIG. 9 is similar to FIG. 8 but with an 8 g ice pellet.
Figure 10:
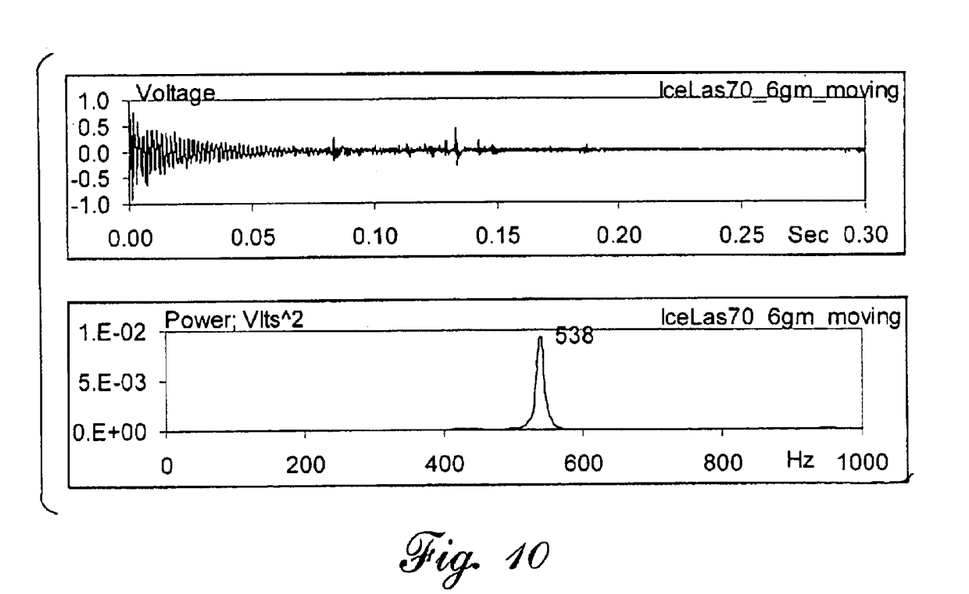
FIG. 10 shows the response using a 6 g ice pellet shot at 480 kPa (70 psig) at a moving log.

In all cases described so far the log was isolated from all movement and vibration. This condition is rarely found in a sawmill or other industrial environment. FIGS. 9 and 10 are the results of an experiment designed to test the effect of log movement on measured resonant frequency. In FIG. 9 an 8 g ice pellet was shot at 415 kPa (60 psi) with the log being motion free. This is compared with the results of FIG. 10 when a 6 g pellet was shot at 480 kPa (70 psi) and the log was manually rocked during the measurement. In both of these tests an accelerometer located against the side of the log was used as the transducer. Results were comparable and the motion did not seriously affect die signal received or the measured resonant frequencies. Similar experiments showed the laser Doppler vibrometer more sensitive to log motion during measurement. Thus, it is preferred that log motion and environmental vibration be minimized using this instrument to detect signal response.

Figure 11:
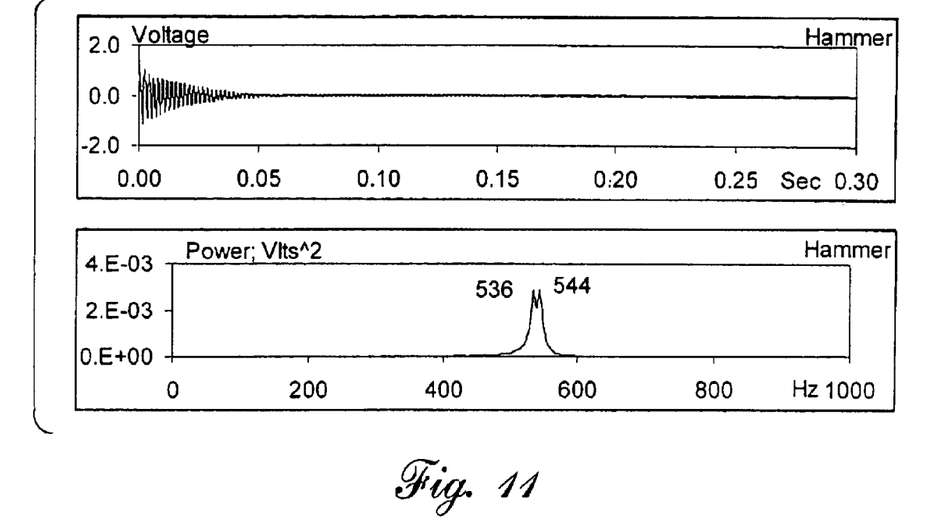
FIGS. 11 and 12 give the response measured respectively on stationary and moving logs with the laser Doppler vibrometer using a hammer impact to initiate the stress wave.
Figure 12:
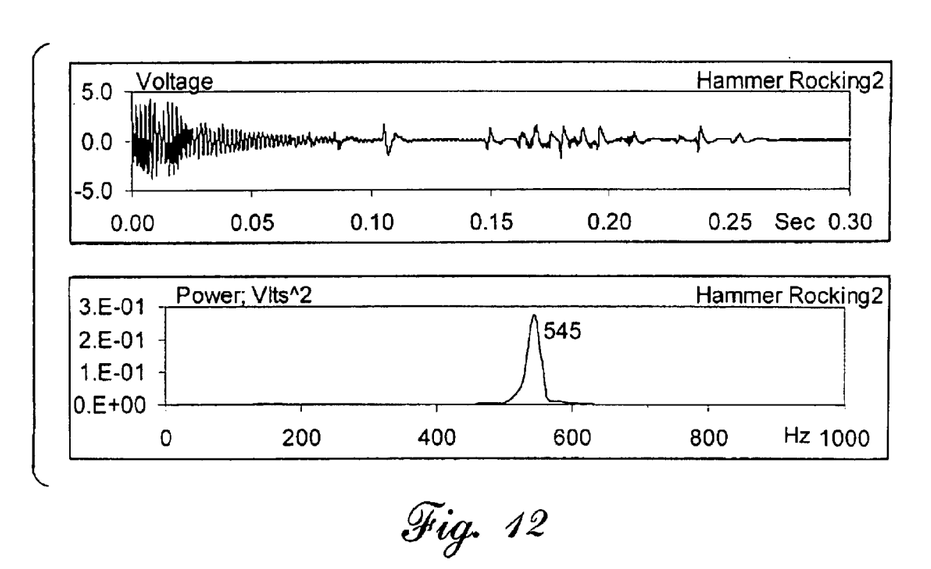

FIGS. 11 and 12 are results of tests similar to those shown in FIGS. 9 and 10 in which a still and rocked log were hit with a hammer to induce the stress wave. The laser vibrometer was again used to measure the resonance frequency. The measured resonant frequency measured in both cases was comparable to that measured under the other conditions. Log motion did not seriously affect the signal received.

In past practice where a pneumatic hammer is used to induce the shock wave, the accelerometer needed to receive the signal is mounted on a swinging arm that moves into and out of contact with the end of the log at the measuring location Other methods of contacting the log with an accelerometer are useful. As one example, the accelerometer may be mounted in a tough, resilient elastomeric belt or sling that the log is rolled into during measurement.

It will be readily apparent to those skilled in the art that either a liquid pulse or a solid pellet directed at the end of a log or other timber member will induce a shock wave that can be readily measured and used to determine at least one physical property of the member. Further, if the log can be held reasonably free of motion, the response can be measured by an instrument such as a laser Doppler vibrometer to achieve a filly non-contact system Even if motion cannot be entirely eliminated, the need for even ending the logs being measured is no longer required.

Knowing the measured physical property, stiffness being an example, the log can then be directed for further processing that will realize optimum value. As an example, the modulus of elasticity may be entered into a cutting optimizer program to determine optimum breakdown of the log, as is described in U.S. Pat. No. 6,026,689.

It will be evident to those skilled in the art that variations in the method described may become apparent that have not been exemplified. It is the intent of the inventors that these variations be included within the scope of the invention if encompassed within the following claims.

What is claimed is:

1. A method of determining a physical property of a log or similar wood member which comprises:

projecting a small amount of a liquid or solid against the end of the log with sufficient energy to initiate a stress wave;

measuring the time of travel of the stress wave in the log; and relating the time of stress wave travel to a physical property of the log.

2. The method of claim 1 in which a pulse of liquid under high pressure is projected to initiate the stress wave.

3. The method of claim 2 in which the liquid is water.

4. The method of claim 3 in which the water includes a surfactant.

5. The method of claim 2 in which the liquid in the liquid pulse has a weight no greater than about 50 g.

6. The method of claim 1 in which a solid pellet is projected against the end of the log.

7. The method of claim 6 in which the pellet is ice.

8. The method of claim 6 in which the solid pellet has a weight no greater than about 10 g.

9. The method of claim 1 in which the time of travel of the stress wave is measured by an accelerometer in contact with the log.

10. The method of claim 1 in which the tie of travel of the stress wave is measured by a non-contact laser Doppler vibrometer.

11. The method of claim 1 in which the physical property measured is modulus of elasticity.

12. The method of claim 11 in which the modulus of elasticity is used in a cutting optimizer program to determine optimum breakdown of the log.

* * * * *